US00PP07948P

United States Patent [19]

Warriner

[11] Patent Number: Plant 7,948

[45] Date of Patent: Aug. 25, 1992

[54] ROSE PLANT JACSHIP

[75] Inventor: William A. Warriner, Tustin, Calif.

[73] Assignee: Bear Creek Gardens, Inc., Medford, Oreg.

[21] Appl. No.: 625,548

[22] Filed: Dec. 10, 1990

[51] Int. Cl.[5] ..... A01H 5/00

[52] U.S. Cl. ..... Plt./1

[58] Field of Search ..... Plt. 1, 9, 26, 27, 28

*Primary Examiner*—Howard J. Locker

*Attorney, Agent, or Firm*—Klarquist, Sparkman, Campbell, Leigh and Whinston

[57] ABSTRACT

A shrub class rose plant having upright, vigorous, dense growth habit, dark green, glossy, disease-resistant foliage, heavy production of small pink flowers and ease of production from hardwood or softwood cuttings.

1 Drawing Sheet

The present invention relates to a new and distinct variety of rose plant of the shrub class which was originated by me by crossing the variety Zorina, U.S. Plant Pat. No. 2,321, with the variety Heidi, U.S. Plant Pat. No. 4,355.

The primary objective of this breeding was to produce a new rose variety having the disease-resistant glossy foliage and upright habit of Zorina combined with the small pink flowers and dense growth habit of Heidi. The objective was substantially achieved along with other desirable improvements as evidenced by the following unique combination of characteristics which are outstanding in the new variety and which distinguish it from its parents, as well as from all other varieties of which I am aware:

1. Upright, vigorous dense growth habit.
2. Dark green, glossy, disease-resistant foliage.
3. Heavy production of small pink flowers.
4. Ease of production from hardwood or softwood cuttings.

Asexual reproduction of this new variety by softwood and hardwood cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with The Royal Horticultural Society (London) Colour Chart, except where ordinary dictionary significance of color is indicated.

Parentage:

*Seed parent.*—Zorina, U.S. Plant Pat. No. 2,321.

*Pollen parent.*—Heidi, U.S. Plant Pat. No. 4,355.

Classification:

*Botanical.*—Rosa hybrida.

*Commercial.*—Shrub.

FLOWER

Observations made from specimens grown in a garden in Somis, Calif. in September, 1990.

Blooming habit: Recurrent.

Bud:

*Size.*—½ to ¾ inches when the petals start to unfurl.

*Form.*—Short, pointed ovoid.

*Color.*—When sepals first divide, bud color is Red Group 48A. When half blown, the upper sides of the petals are Red Group 48C; and the lower sides of the petals are Red Group 48C.

*Sepals.*—Color: Green Group 138C but often with a bronze cast. Surface texture: Covered with fine hairs. There are three normally appendaged sepals that are edged with glands. There are two unappendaged sepals with hairy edges.

*Receptacle.*—Color: Green Group 143C. Shape: Funnel. Size: Small (¼×¼"). Surface: Smooth.

*Peduncle.*—Length: Short (1½ to 1¾"). Surface: Glandular. Color: Bronzy. Strength: Stiff, erect, slender.

Bloom:

*Size.*—Small. Average open size is 2 inches.

*Borne.*—Singly and several together, in pyramidal clusters.

*Stems.*—Short (10 to 12"), strong.

*Form.*—When first open: High center. Permanence: Retains its form to the end, outer petals curl back, quill fashion.

*Petalage.*—Number of petals under normal conditions: 30 to 35.

*Color.*—The upper side of the petals is Red Group 48C. The reverse side of the petals is Red Group 48C. The base of each petal has a Yellow half moon at the point of attachment (3/16"×4/16"). The major color on the upper side is Red Group 48C.

*Variegations.*—None.

*Discoloration.*—No change in general tonality at the end of the first day or at the end of the third day.

*Fragrance.*—Slight.

Petals:

*Texture.*—Thick.

*Shape.*—Round.

*Form.*—Tips slightly recurved, edges slightly quilled.

*Arrangement.*—Imbricated. Petaloids in the center: Few.

*Persistence.*—Drop off cleanly.

*Lastingness.*—On the plant: Long (5 to 7 days). As a cut flower; Long (7 days).

Reproductive parts:

*Anthers.*—Size: Medium. Quantity: Many. Color: Yellow. Arrangement: Regular around styles.

*Filaments.*—Color: Yellow.

*Pollen.*—Color: Gold yellow.

*Styles.*—Color: Greenish white.

*Stigmas.*—Color: Greenish white.

Form: Shrub.

Growth: Very vigorous, upright, branching. Grows to 5′ in California.

Foliage: Number of leaflets on normal mid-stem leaves; 5, occasionally 6 or 7.

*Size.*—Small (3″×2″).

*Quantity.*—Abundant.

*Color.*—New foliage: Reddish. Old foliage: Dark glossy green.

Leaflets:

*Shape.*—Pointed oval.

*Texture.*—Upper side: Leathery, glossy.

*Edge.*—Serrated.

*Serration.*—Single, small.

*Petiole rachis.*—Color: Reddish.

*Petiole underside.*—Rough, with prickles.

*Stipules.*—Long for the size of the leaf (¾″), bearded.

*Disease resistance.*—Resistant to mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—Many on main canes from base and on laterals from main canes.

*Form.*—Short (¼″), hooked slightly downward.

*Color when young.*—Red.

Small prickles:

*Quantity.*—On main stalks: Many. On laterals: Few.

*Color.*—Brown.

I claim:

1. A new and distinct variety of rose plant of the shrub class, substantially as herein shown and described, characterized particularly as to novelty by the unique combination of its small, pink, abundant, miniature-like flowers borne on a vigorous, dense, upright-growing shrub, its disease-resistant, dark green, glossy foliage and its ease of production from softwood or hardwood cuttings.

* * * * *

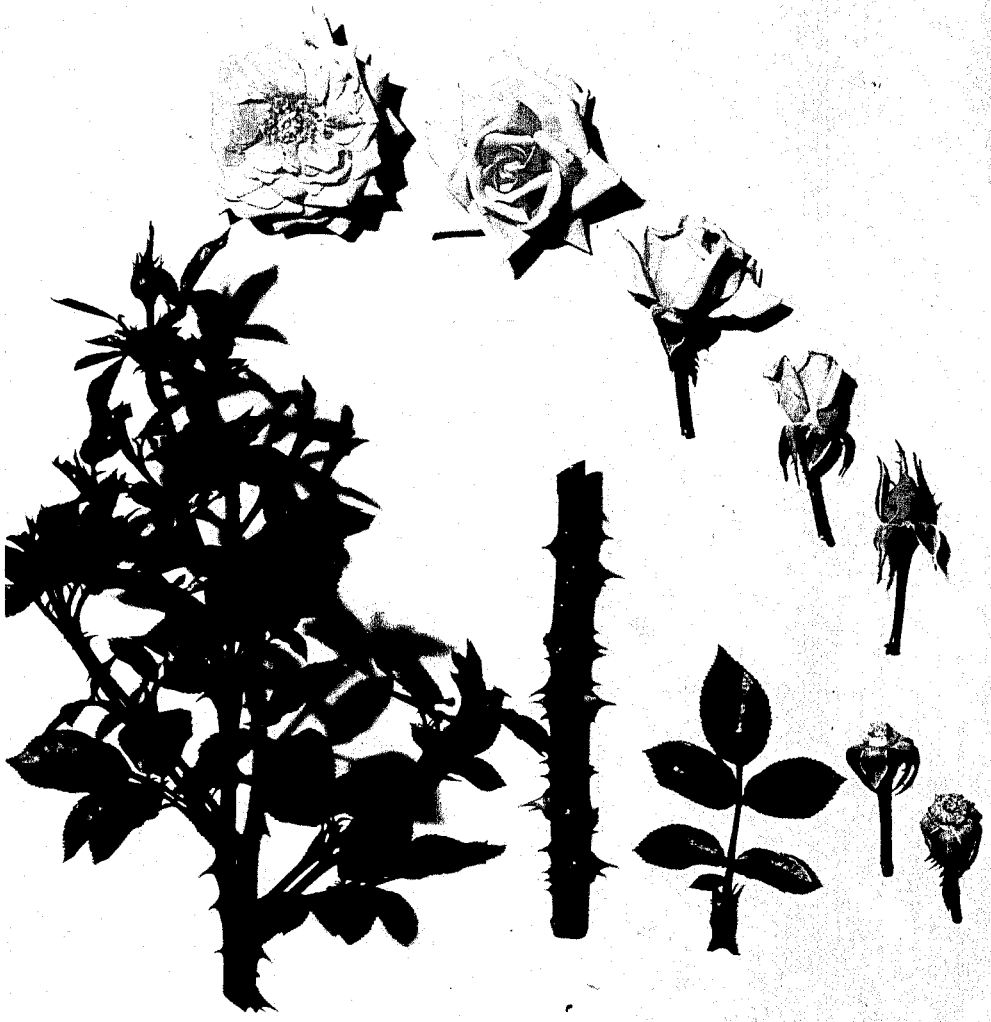
JACship